(12) United States Patent
Sidebotham et al.

(10) Patent No.: US 9,101,368 B2
(45) Date of Patent: Aug. 11, 2015

(54) METHODS OF FORMING MEDICAL REAMERS

(71) Applicants: Christopher G. Sidebotham, Mendham, NJ (US); Leon Roitburg, East Hanover, NJ (US); Randall J. Lewis, Bethesda, MD (US)

(72) Inventors: Christopher G. Sidebotham, Mendham, NJ (US); Leon Roitburg, East Hanover, NJ (US); Randall J. Lewis, Bethesda, MD (US)

( * ) Notice: Subject to any disclaimer, the term of this patent is extended or adjusted under 35 U.S.C. 154(b) by 58 days.

(21) Appl. No.: 13/741,211

(22) Filed: Jan. 14, 2013

(65) Prior Publication Data

US 2013/0245628 A1 Sep. 19, 2013

Related U.S. Application Data

(60) Provisional application No. 61/586,685, filed on Jan. 13, 2012.

(51) Int. Cl.
| | |
|---|---|
| *A61B 17/16* | (2006.01) |
| *B23P 15/46* | (2006.01) |
| *B23K 26/00* | (2014.01) |
| *A61B 17/00* | (2006.01) |

(52) U.S. Cl.
CPC ............ *A61B 17/1615* (2013.01); *A61B 17/16* (2013.01); *A61B 17/1666* (2013.01); *B23K 26/0093* (2013.01); *B23P 15/46* (2013.01); *A61B 17/164* (2013.01); *A61B 17/1677* (2013.01); *A61B 2017/00526* (2013.01)

(58) Field of Classification Search
CPC ........... A61B 17/1615; A61B 17/1666; A61B 17/16; A61B 17/164; A61B 17/1677; A61B 2017/00526; B23K 26/0093; B23P 15/46

USPC .............. 29/462, 448, 527.1, 527.4, DIG. 67; 606/81, 79, 80, 180; 76/115; 219/121.64

See application file for complete search history.

(56) References Cited

U.S. PATENT DOCUMENTS

| | | | |
|---|---|---|---|
| 1,916,874 A | 7/1933 | Wilhelm | |
| 6,764,490 B1 | 7/2004 | Szabo | |
| 7,011,662 B2 * | 3/2006 | Lechot et al. | 606/80 |
| 2003/0135219 A1 | 7/2003 | Salyer et al. | |
| 2006/0217730 A1* | 9/2006 | Termanini | 606/81 |
| 2007/0276393 A1* | 11/2007 | Bonadei | 606/80 |
| 2008/0215159 A1* | 9/2008 | Stamp | 623/22.21 |
| 2008/0306482 A1 | 12/2008 | Muller | |
| 2010/0145342 A1 | 6/2010 | Grace et al. | |
| 2010/0292699 A1* | 11/2010 | Favre | 606/80 |
| 2011/0202060 A1* | 8/2011 | White et al. | 606/80 |

FOREIGN PATENT DOCUMENTS

| | | |
|---|---|---|
| DE | 10 2005 058107 | 7/2007 |
| EP | 2 359 755 | 8/2011 |

OTHER PUBLICATIONS

International Search Report from PCT Application No. PCT/US2013/021473 dated Jun. 20, 2013.
Written Opinion of the International Search Authority from PCT Application No. PCT/US2013/021473 dated Jun. 20, 2013.

* cited by examiner

*Primary Examiner* — Sarang Afzali
(74) *Attorney, Agent, or Firm* — Klarquist Sparkman, LLP

(57) ABSTRACT

A cutting tool is provided with a cutting surface on a first side of the cutting tool and an attachment member on a second side of the cutting tool. The cutting surface can have cutting edges with characteristics that vary along the cutting tool. Novel methods of manufacturing such cutting tools are also provided.

14 Claims, 16 Drawing Sheets

Hollow Spherical Reamers:
*acetabulum preparation*

Hollow Tapered Reamers:
*Intramedullary canal of bones*

Hollow Cylindrical Reamers:
*Intramedullary canal of bones*

Hollow Flat Reamers:
*patella articular surface*

METHODS OF FORMING MEDICAL REAMERS

CROSS REFERENCE TO RELATED APPLICATION

This application claims the benefit of U.S. Provisional Application No. 61/586,685, which was filed on Jan. 13, 2012, and is incorporated herein by reference in its entirety.

FIELD

This disclosure relates to a novel systems and method relating to cutting tools.

BACKGROUND

Cutting tools, such as medical reamers used by surgeons, generally have a cutting surface that is able to cut and/or remove material from an object. For example, in many different disciplines in orthopedics cutting tools are used for machining bone in the preparation of artificial joints including hips, knees, elbows and shoulders, and also in the repair of long bone fractures. The design and method of manufacturing cutting surfaces of cutting tools can affect the efficiency, functional life of the spherical reamer and cost in manufacturing. Accordingly, improvements relating to design and manufacturing methods are desirable.

SUMMARY

In some embodiments, improved cutting tools and methods of manufacturing the same are provided.

In certain implementations, the cutting tools comprise medical reamers, including acetabular reamers, long bone cylindrical reamers, long bone tapered reamers, patella reamers and glenoid reamers along with the design of different cutting teeth in specific zones of the reamers and the improved method of making these reamers and their cutting edges.

In some implementations, a cutting tool is provided with a cutting surface on a first side of the cutting tool and an attachment member on a second side of the cutting tool. The cutting surface can include a plurality of cutting edges and the attachment member can be configured to be coupled to a powered driving member (e.g., a drill). The cutting tool comprises an axis of rotation and the cutting surface defines a plurality of latitude lines. The plurality of cutting edges can be oriented at varying orientation angles relative to the latitude lines.

In some implementations, the plurality of cutting edges can be in three different zones and respective cutting edges in the different zones have different characteristics. The different zones can comprise a polar zone, a transition zone, and an equatorial zone. Respective cutting edges can define a cutting angle between the cutting edge and a first side of the cutting tool, and the cutting angle between cutting edges in the polar zone can be larger than those defined by cutting edges in the transition zone, and the cutting angle between cutting edges in the transition zone can be larger than those defined by cutting edges in the equatorial zone. In some implementations, the tooth height can be the same (i.e., substantially the same) regardless of the cutting angle.

In some implementations, the orientation angles vary depending on whether the respective cutting edges are in the polar zone, the transition zone, or the equatorial zone, and the orientation angle of respective cutting edges in the equatorial zone is greater than the orientation angle of respective cutting edges in the transition zone, and the orientation angle of respective cutting edges in the transition zone is greater than the orientation angle of respective cutting edges in the polar zone.

In some implementations, the thickness of the side wall is less than 0.040 inches, or in some cases, between 0.022 inches and 0.40 inches. Openings can be provided adjacent respective cutting edges, the respective openings defining a funnel angle that is between 20 and 40 degrees. In some cases, the funnel angle can be between 25 and 35 degrees.

In some implementations, the cutting surface is a panel and the cutting tool comprises a plurality of separate panels. The cutting tool can include a frame member (e.g., a center support and a base) and the plurality of separate panels can be coupled to the frame member.

In another implementation, a method for forming a cutting tool is provided. The method can include forming a plurality of panels from one or more flat sheets of metal and coupling the plurality of panels to a frame member to form the cutting tool. The plurality of panels can be formed with a plurality of cutting edges and a plurality of openings adjacent respective cutting edges. When coupled to the frame member, the plurality of panels can define a plurality of latitude lines about the axis of rotation of the cutting tool and the plurality of formed cutting edges have orientation angles relative to the latitude lines that vary. In some cases, respective panels can have cutting edges with orientation angles that vary along the respective panel.

In certain implementations, the act of forming a plurality of panels comprises stamping the one or more flat sheets of metal to form a plurality of cavities and punching holes at or adjacent to the plurality of cavity to provide bone-chip-receiving openings. The act of forming the plurality of cavities can include forming a plurality of "V"-shaped cavities.

In certain implementations, the act of forming the plurality of panels can include stamping the one or more panels to create a desired height of the cutting edges and to provide a desired curvature of the one or more panels.

In certain implementations, the act of coupling the plurality of panels to the frame member can include forming a frame member that comprises a center support, a base, and a form dome, and securing the plurality of panels to the center support, the base, and the form dome. In some cases, the act of securing the plurality of panels to the center support, the base, and the form dome can be performed by laser welding or other types of welding. The act of coupling the plurality of panels to the frame member can also include placing the plurality of panels into an injection molding tool and injection molding the frame member around the plurality of panels to create the frame member.

In some implementations, the act of forming a plurality of panels from one or more flat sheets of metal can include forming the plurality of cutting edges with different zones that have cutting edges with different characteristics, the different zones comprising a polar zone, a transition zone, and an equatorial zone. Respective cutting edges can define a cutting angle between the cutting edge and a first side of the cutting tool, and the cutting angle between cutting edges in the polar zone are larger than those defined by cutting edges in the transition zone, and the cutting angle between cutting edges in the transition zone are larger than those defined by cutting edges in the equatorial zone.

In certain implementations, the act of punching holes at or adjacent to the plurality of cavity comprises forming bone-chip-receiving openings with a funnel angle that is between 20 and 40 degrees. In addition, in some cases, the one or more flat sheets of metal have a thickness less than 0.040 inches.

In certain implementations, the method includes determining an effective functional life of the cutting tool.

In other embodiments, a cutting tool is provide that has a cutting surface on a first side of the cutting tool, the cutting surface comprising a plurality of cutting edges, and an attachment member on a second side of the cutting tool, the attachment member being configured to be coupled to a powered driving member. A plurality of cutting edges are provided in at least three different zones and respective cutting edges in the different zones have different characteristics.

The foregoing and other objects, features, and advantages of the invention will become more apparent from the following detailed description, which proceeds with reference to the accompanying figures.

DETAILED DESCRIPTION

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

As used herein, the term "effective functional life" means the amount of use a tool can experience before it begins to operate suboptimally for its intended purpose. In some embodiments, the effective functional life can be based on a number of uses of the tool and/or an amount of time the tool has been used. As used herein, the term "single-use" tool or instrument means a tool or instrument that is configured and/or intended to be used once before being discarded. Thus, a single-use tool or instrument is a non-reusable device in contrast to reusable tools or instruments which, subject to certain procedures such as cleaning and sterilization, may be used more than once. As used herein, the term "powered driving member" means any device capable of driving a cutting tool such as, for example, a drill.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Figure 1:
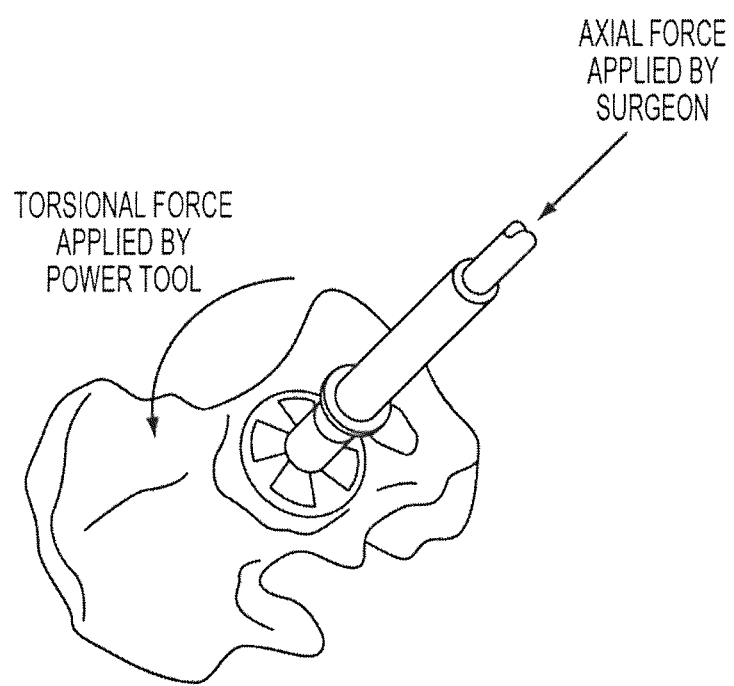
FIG. 1 illustrates an acetabular reamer, the use of the reamer to prepare the acetabulum, and a press-fit acetabular implant positioned as part of a total hip procedure.

It is generally desirable that cutting surfaces on a cutting tool (e.g., cutting teeth) be as accurate and consistent as possible for the dimensional accuracy of the final preparation in the bone. For example, cementless acetabular implants (press fit) are dependent on their dimension and the dimension of the bone preparation to create a reproducible interference fit for establishing initial stability of the implant. FIG. 1 illustrates an acetabular reamer, the use of the reamer to prepare the acetabulum, and a press-fit acetabular implant positioned as part of a total hip procedure.

The initial stability of the implant is critical to long term success and if the implant moves large amounts (e.g., 75 microns or more) under physiological loads post-operatively, it can result in soft tissue growing into the implant rather than bone. If this occurs, the implant will eventually loosen. Accordingly, the accuracy of the initial fit must provide stability of the implant to allow bone to grow into the implant during the first 6-12 weeks after surgery. In some instances, the interference level required for cementless acetabular implants can be required to be very small (e.g., less than 2 mm, and, in some cases, preferably less than 1 mm). However, commercial cutters can vary in their accuracy by as much as 0.25 mm and these variations can result in initial acetabular implant stability. Because the initial interference fit provides stability to the implant, improved accuracy of the teeth height and performance can assist in achieving this goal.

Configuration of Cutting Members

Conventional reamer designs use the same cutting tooth geometry within each design. These teeth are also positioned at 90° to the latitude lines of the spherical reamer surface. However, cutting teeth around the equator of the reamer perform a side cutting function while teeth towards the dome of the cutter perform an end cutting function.

As described in more detail herein, various embodiments are provided in which reamers utilize different cutting teeth configurations and different orientations to address the different bone cutting requirements and thereby improving the efficiency of the cut. By efficiently designing cutting teeth for specific operations, faster bone cuts can be achieved, thereby producing less friction. Minimizing the friction generated by the reamers relates directly to maintaining the life of the bone. Friction can lead to heat and if the cutter-bone interface reaches temperatures above 50° C. (122° F.) bone death (necrosis) can occur. This can affect long term success of the procedure whether the implant is used with or without bone cement. If the bone preparation bed is damaged due to excessive heat generated from the acetabular cutter, the fixation of the implant will be compromised and can lead to loosening and revision.

Figure 2:
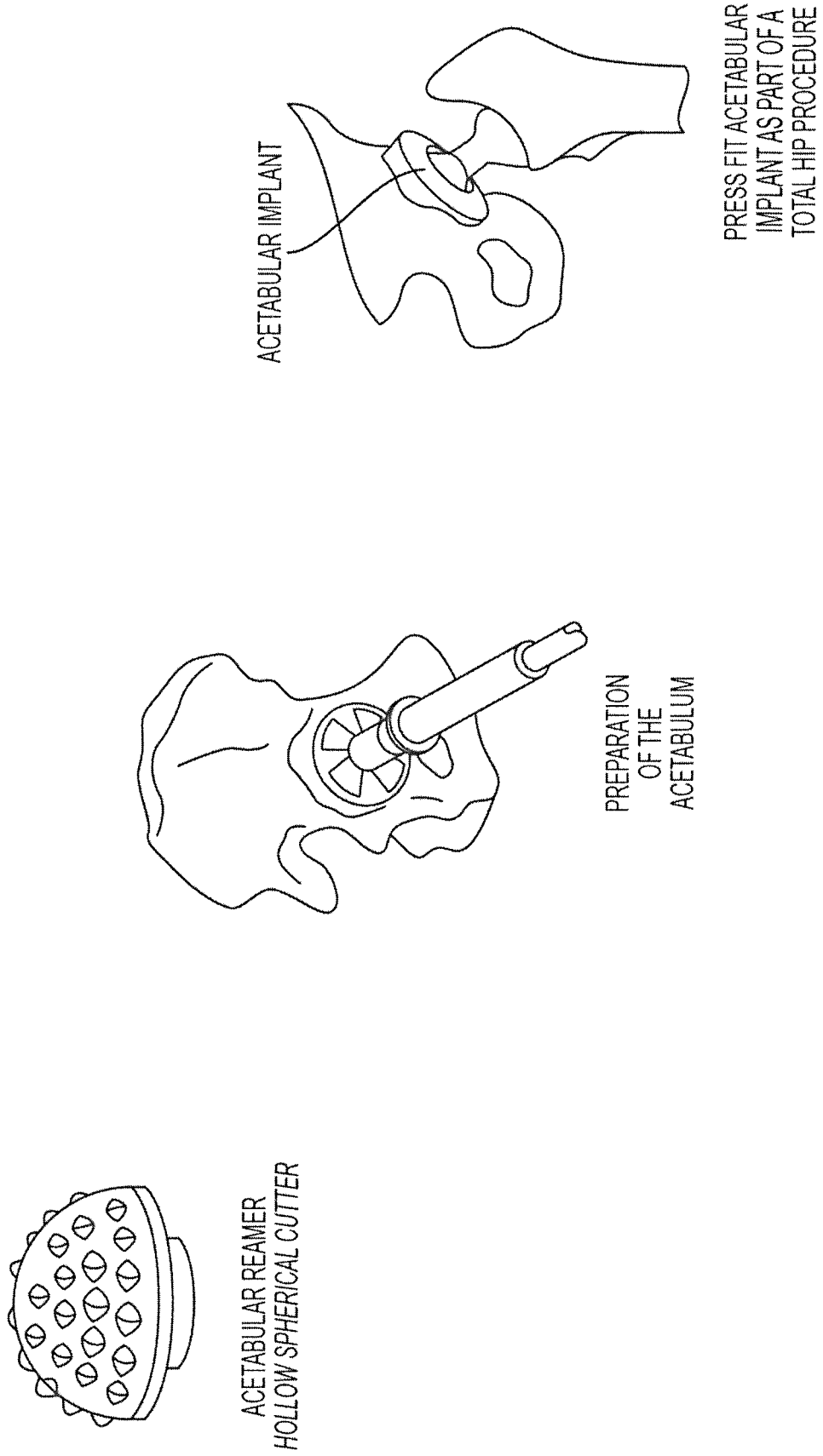
FIG. 2 illustrates axial force applied by a surgeon, by pushing the cutter into the acetabulum and a second torsional force exerted by the power reaming tool.

There are two primary forces applied to the reamer during the machining of the bone. When considering an acetabular reamer, as shown in FIG. 2, there is an axial force applied by the surgeon who pushes the cutter into the acetabulum and a second torsional force exerted by the power reaming tool. In some embodiments, the novel cutting tools disclosed herein convert the torsional force into a force applied at the cutting tooth edge to improve the efficiency of the cut.

The systems and methods described herein for forming cutting tools can provide greater control and accuracy of the tooth sharpness, cutting angles, and resulting bone chip removal by the tool. In addition, as described in more detail below, the cutting tools described herein can be formed by novel manufacturing processes that permit the creation of multiple teeth in one operation.

Figure 3:
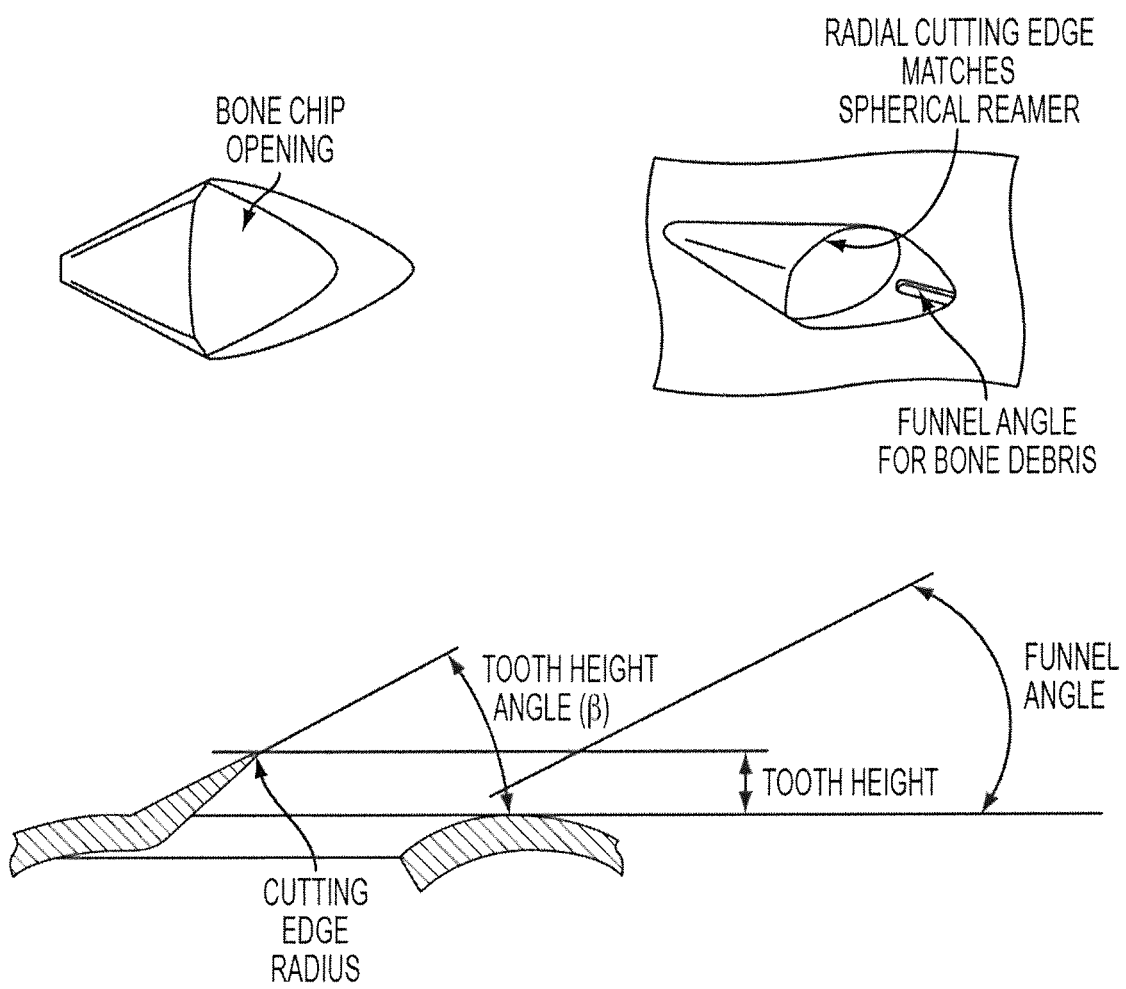
FIG. 3 illustrates a cutting tool composed of a sharp tooth edge, a specific tooth elevation, specific cutting angle, a specific tooth orientation to the axis of rotation and a peripheral opening around the cutting edge providing an improved flow path for the bone debris.
Figure 4:
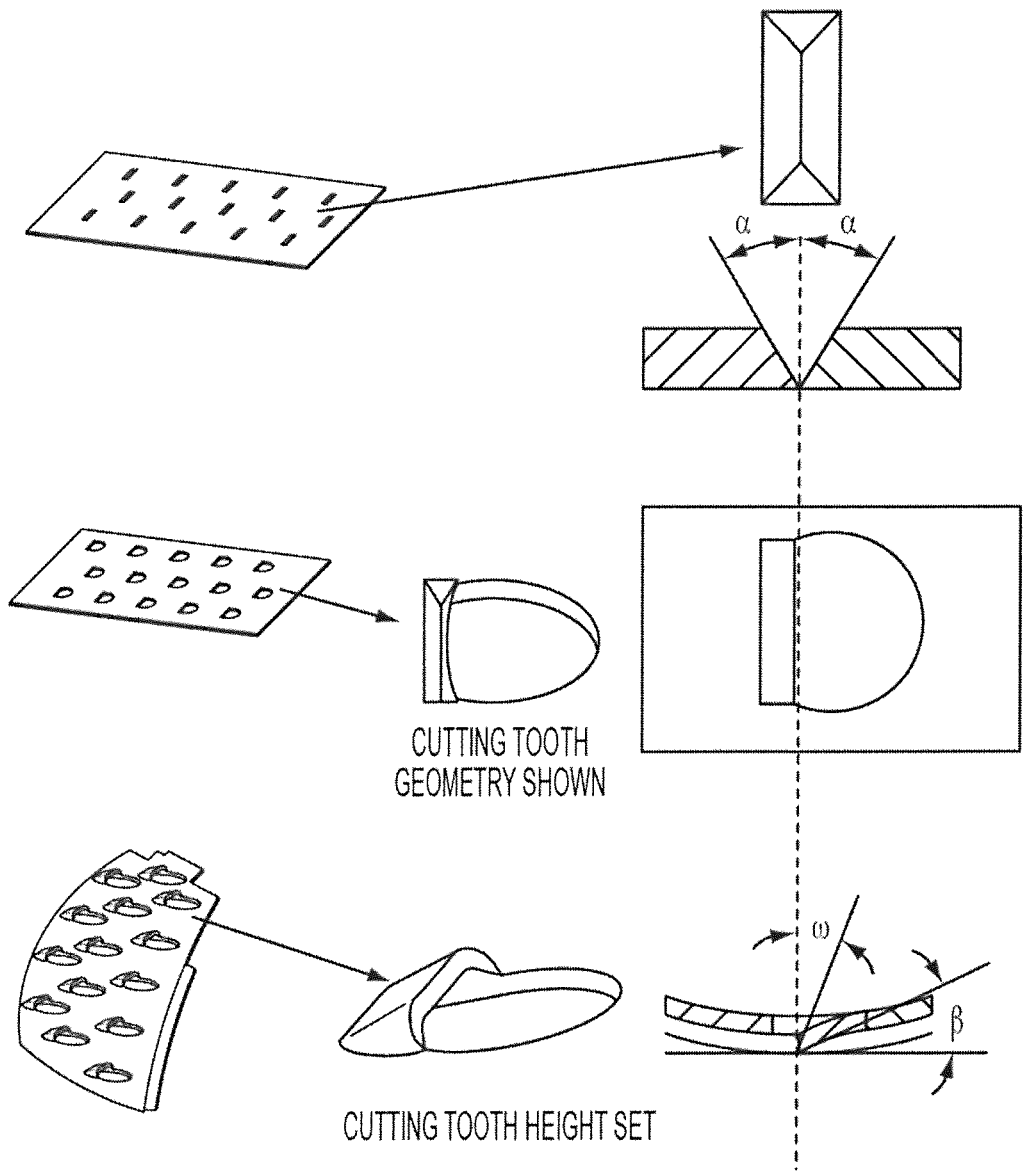
FIG. 4 illustrates another way of manufacture of cutting teeth geometry.

In the embodiments described herein, cutting surfaces (e.g., teeth) can comprise a sharp tooth edge (tolerance 0.0005" to 0.002" tooth edge radius), a specific tooth elevation (tolerance 0.002"-0.004"), specific cutting angle, a specific tooth orientation to the axis of rotation (e.g., tool angle), and a peripheral opening around the cutting edge providing a designed flow path for the bone debris as shown in FIG. 3. This tooth geometry can also be manufactured according to FIG. 4 through a series of stamping operations allowing for multiple teeth to be made at the same time. For example, as illustrated in FIG. 4, a flat sheet of material (e.g., metal) can be stamped so that a plurality of "V"-type cavities are punched into the sheet based on a desired cutting angle ω. Next, a plurality of holes can be punched around the "V"-type cavities (or grooves), creating a cutting edge. If necessary, another stamping step can be performed to stamp the tooth height and curvature in operation (or multiple operations if desired). As shown in FIG. 4, angle β determines the tooth height and angle β in conjunction with angle α will determine the rake angle ω (ω=α−β) of the cutting surface. In some embodiments, the rake angle can vary between about 5 and 25 degrees, and in other embodiments between about 5 and 15 degrees (e.g., about 10 degrees)

Thus, in contrast to conventional devices, the tooth angle (α) can be established in the first forming operation and can be set (ω and β angles) based on the intended function. Multiple iterations of this tooth design can be provided in specific zones of the reamer surface which address the intended type of cutting required at those locations.

Figure 5:
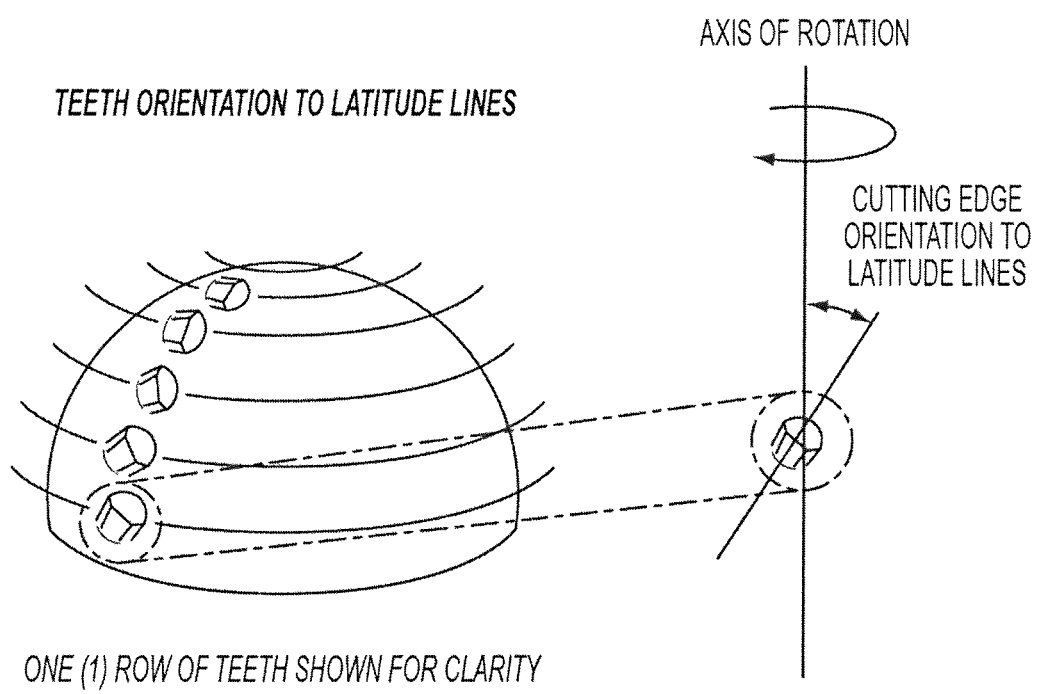
FIG. 5 illustrates a novel cutting tool having a plurality of teeth.
Figure 6:
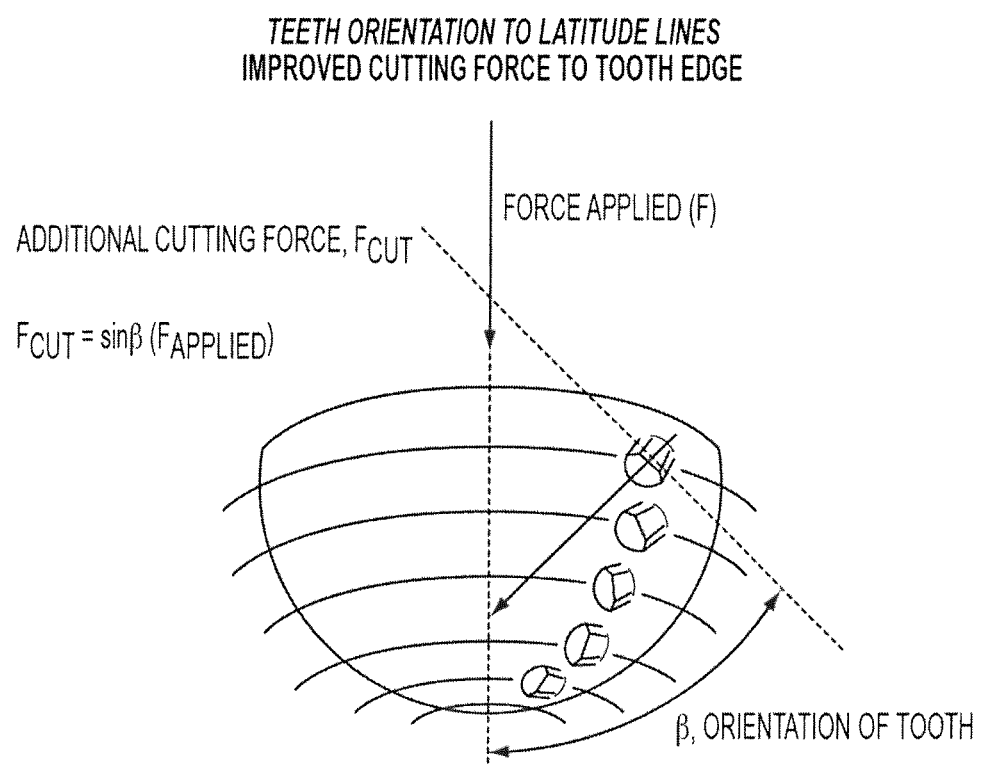
FIG. 6 illustrates a novel cutting tool having a plurality of teeth.

In some embodiments, the novel cutting tools disclosed herein can have teeth arranged in a spiral or helix manner on the surface of the cutter. However, the tooth designs and tooth orientations can be optimized to reduce the reaming time required to complete the preparation. As shown in FIGS. 5-8, the cutting edges of the teeth can be oriented at different angles to the lines of latitude based on the required cutting functions at various positions on the surface of the reamer. This can provide for a faster cut by converting the rotational energy into linear energy assisting in advancing the reamer into the preparation analogous to a screw thread (FIG. 5). The tooth orientation can further improve the cutting force at the tooth edge. By changing the orientation of the cutting edge relative to the latitude lines, a portion of the torsional force is converted into a cutting force at the tooth edge as shown in FIG. 6. This improvement primarily benefits the teeth closest to the equator as they are performing a side cutting function.

As shown in FIGS. 5-6, the angle of orientation of the cutting edge relative to axis of rotation can increase from the equatorial teeth to the polar teeth and decrease relative to the latitude lines. At least three different types of cutting teeth (e.g., orientation angles and/or cutting angles varying) can be provided on the tool. In some embodiments, at least three regions are provided with similar type teeth in each region. In other embodiments, the teeth can vary in a transitional manner effectively providing more than three zones.

In some embodiments, relative to the latitude lines, the range of variation can be orientation angles of between 10 and 30 degrees (more preferably between 15 and 25 degrees—e.g., 20 degrees) for the equatorial zone, orientation angles of less than 5 degrees (more preferably about 0 degrees) in the polar zone, and somewhere in between for the orientation angles in the transition zone (e.g., between 0 and 20 degrees, or preferably between 5 and 15 degrees—e.g., 10 degrees). A benefit of the larger orientation angles in the equatorial zone is a portion of the axial load applied by the operator will be converted into driving the cutting edge into the bone. As you move to the polar zone, the angle of the tooth on the surface has less effect as the tooth becomes perpendicular to the direction of the cut. That is, the specific tooth geometry in the polar zone needs to address an end cutting ability rather than a side cutting ability.

Figure 7:
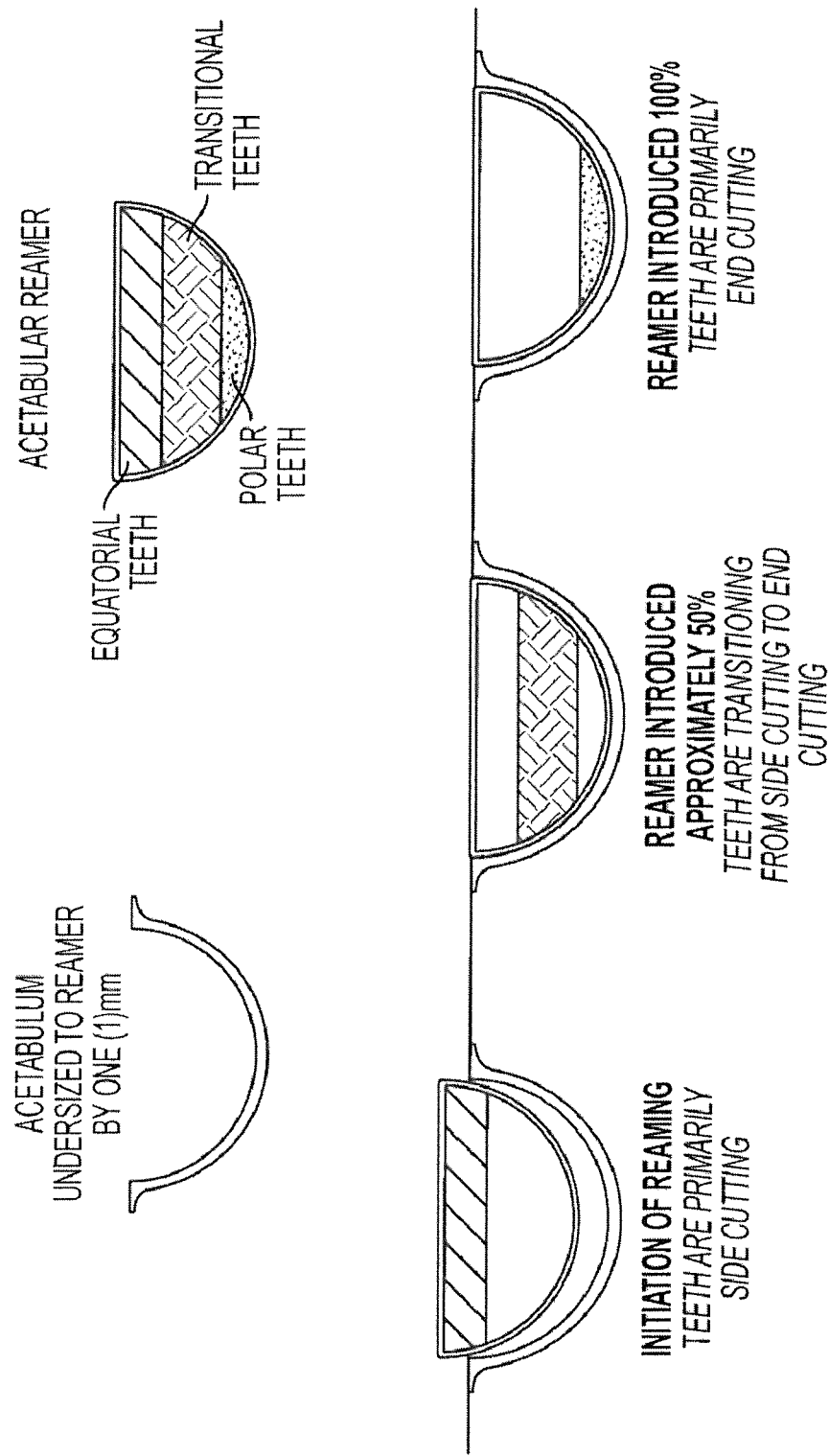
FIG. 7 illustrates a schematic view of cutting teeth zones and their general functions.

FIG. 7 illustrates an exemplary process by which a cutting tool (e.g., a spherical reamer) transitions from engagement with the bone at one area to another area of the cutting tool. As used herein, the term "polar teeth" refer to cutting surfaces at and/or adjacent the pole of the spherical reamer, the term "equatorial teeth" refer to cutting surfaces at and/or adjacent to the equator of reamers having a hemispherical shape (e.g., the area furthest from the poles in FIG. 7), and the term "transition teeth" refer to cutting surfaces between the polar and equatorial teeth.

In the exemplary reaming process illustrated in FIG. 7, the spherical reamer begins by introduction into the concave surface of the acetabulum. It is noted that this initiation of the cut involves just the equatorial teeth. These equatorial teeth are performing more of a side cutting function and therefore can have a specific tooth angle based on this intended function. Additional teeth (i.e., the transitional teeth) become engaged with the bone as the reamer is further introduced into the acetabulum. The transitional teeth perform a combination of side-cutting and end-cutting and can be optimized for this purpose. As the reamer becomes fully inserted into the preparation site, the teeth at the pole (i.e., the polar teeth) of the reamer serve to primarily end-cut.

Figure 8:
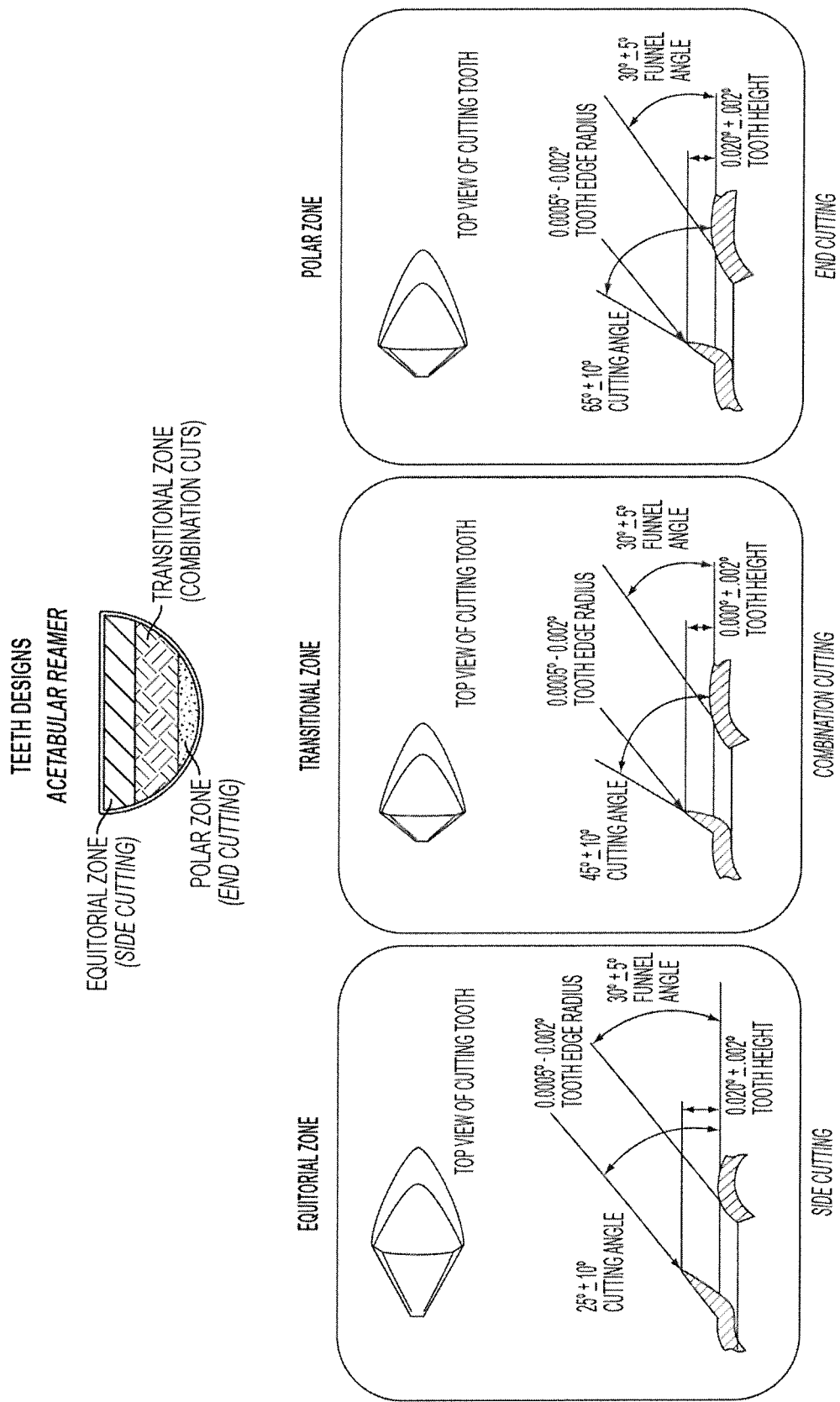
FIG. 8 illustrates a schematic view of cutting teeth zones and their general functions.

Thus, the teeth can have different cutting demands depending on their location on the surface of the reamer and can be configured accordingly. FIG. 8 illustrates the manner in which the cutting angles of the teeth can vary in accordance with the required cutting function of the bone. The table below illustrates the types of teeth and their configurations as reflected in FIG. 8.

| Teeth Region | Cutting angle (defined relative to a side surface of the cutting tool) | Tooth edge radius | Funnel angle | Tooth height |
|---|---|---|---|---|
| Equatorial | 15-35 degrees (more preferably, 20-30 degrees) | 0.0005-0.002" | 20-40 degrees, (more preferably, 25-35 degrees) | 0.020 ± 0.002" |
| Transition | 35-55 degrees (more preferably, 40-50 degrees) | 0.0005-0.002" | 20-40 degrees, (more preferably, 25-35 degrees) | 0.020 ± 0.002" |
| Polar | 55-75 degrees (more preferably, 60-70 degrees) | 0.0005-0.002" | 20-40 degrees, (more preferably, 25-35 degrees) | 0.020 ± 0.002" |

Although, FIG. 8 illustrates these three zones as distinct zones, it should be understood that the cutting surfaces can transition gradually from one zone to another. Thus, polar teeth can transition gradually from polar teeth with the orientation and characteristics noted above to transition teeth with the orientation and characteristics noted above. In this manner, for example, some teeth can have orientation and characteristics of polar teeth (e.g., 65 degree cutting angle), some can have characteristics of transition teeth (e.g., 45 degree cutting angle), and some teeth between the polar teeth and transition teeth can have characteristics somewhere inbetween (e.g., 55 degree cutting angle).

Proper bone chip exit paths can also contribute to an improved surgical preparation. With a non-impeded path for the bone chips to travel away from the cutter, it enables the instrument to produce a faster and cooler bone cut. As shown in FIG. 3, openings can be provided adjacent cutting surfaces to provide a "funnel" that permits bone chips to efficiently flow from the face of the reamer to avoid additional torque requirements to drive the cutter. Without such openings, increased torque is required to drive the cutting tool and such increased torque is usually accompanied by increased axial pressure as the operator senses the resistance in advancing the cutter and applies increased loads. This combination generates increased heat through friction capable of generating temperatures which can cause bone necrosis.

Manufacturing of Cutting Tools

Figure 9:
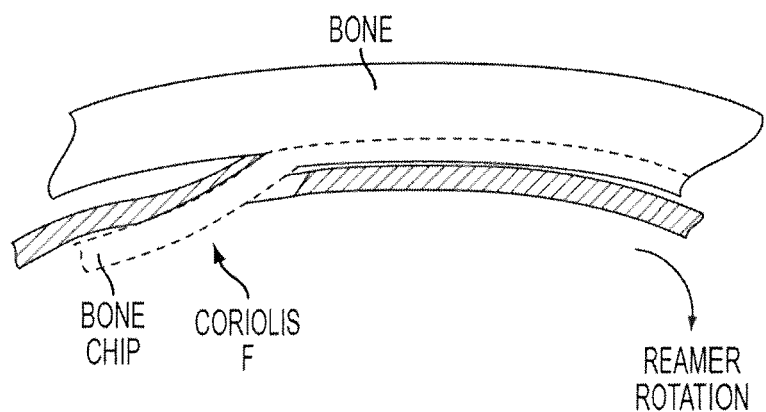
FIG. 9 illustrates a schematic view of cutting forces applied by a cutting tool.

In some embodiments, the novel cutting tools can be manufactured by forming the spherical body and teeth from thinner sheet metal, 0.005"-0.020", which can improve the efficiency in manufacturing (longer tool life of the forming tools) and ability to create a sharp tooth edge without a specific sharpening operation. In addition the thinner material better dissipates the heat generated from the friction of cutting the bone over a thicker walled, heavier mass reamer. The thinner material also produces less friction, therefore a lower temperature at the surface, through reduction of the Coriolis forces (FIG. 9).

Figure 10:
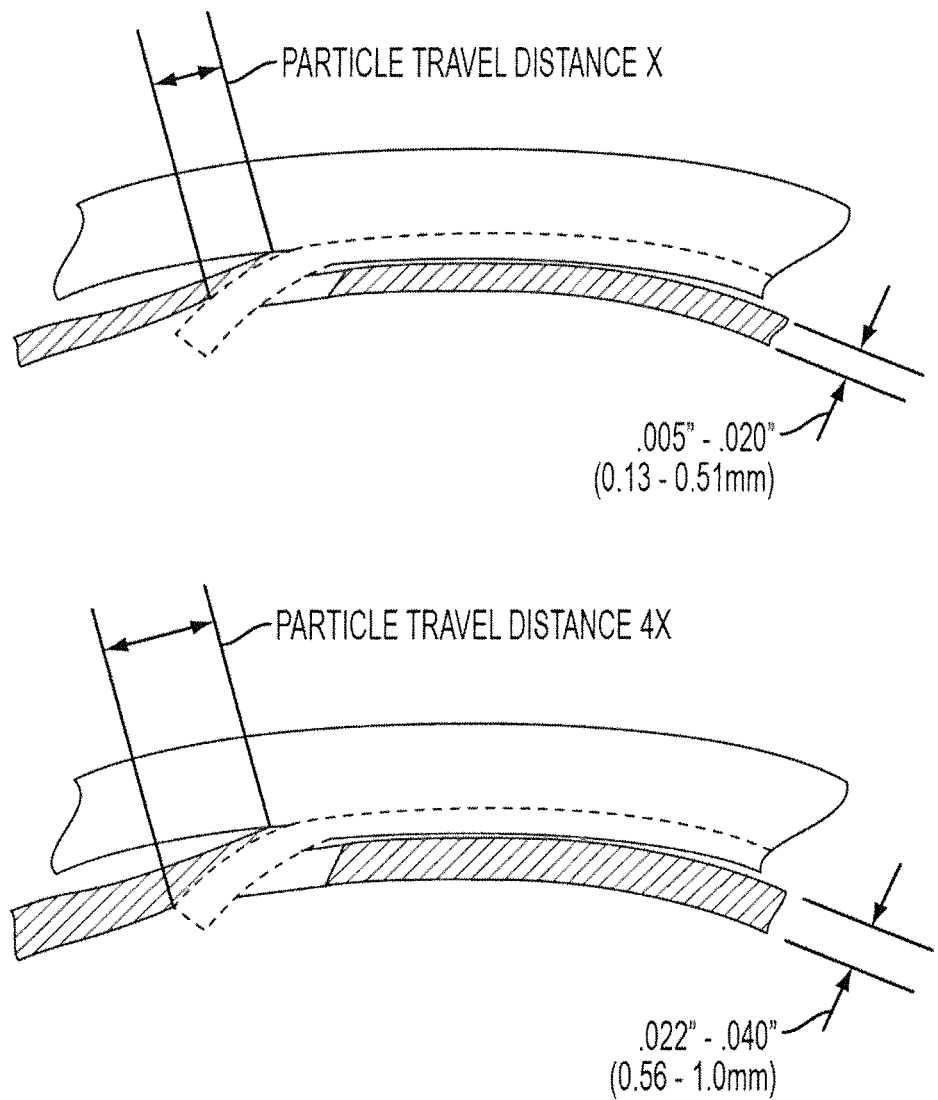
FIG. 10 illustrates a comparison of the frictional forces associated with bone chips created by cutting tools having different thicknesses.

FIG. 10 illustrates a comparison of the frictional forces associated with bone chips created by cutting tools having different thicknesses. As shown in FIG. 10, for thicker walled cutters (e.g., cutters with wall thicknesses greater than 0.22"), the bone chip particles must travel a greater distance in contact with the cutting surface of the cutter. As a result, lower temperatures can be achieved by producing cutters with wall thickness of between 0.005" and 0.020". The following novel manufacturing methods can be used to produce cutting tools with such reduced wall thicknesses.

Figure 11:
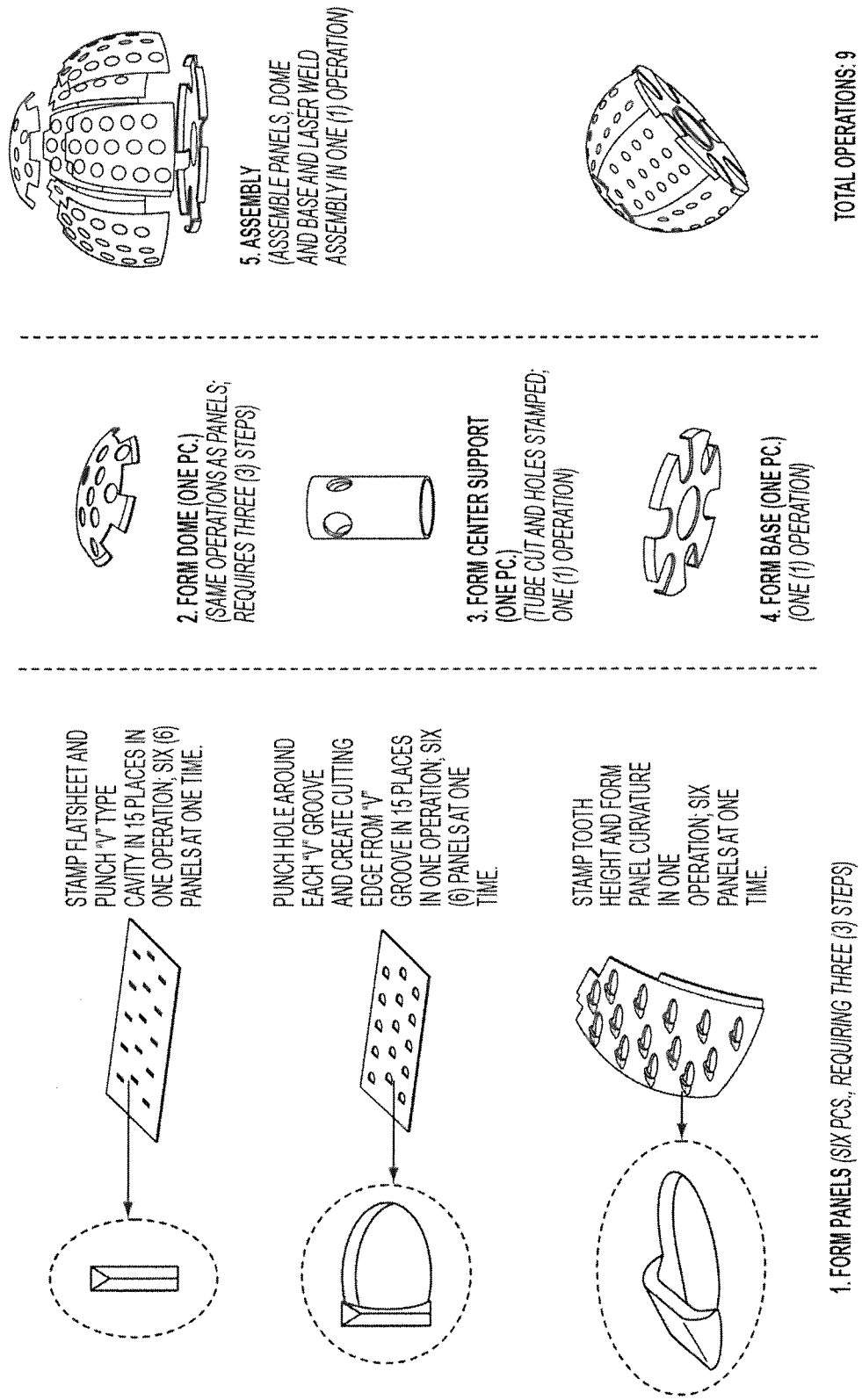
FIG. 11 illustrates exemplary operations for forming panels with multiple teeth designs and assembling such panels into a reamer.

FIG. 11 illustrates exemplary operations for manufacturing cutting tools. As shown in FIG. 11, panels can be formed with multiple teeth designs and a reamer can be assembled as shown. This design and method of manufacturing a spherical reamer can be faster and more efficient than conventional techniques. In some embodiments, this method can be produced in fewer steps, such as in nine operations. In comparison, some conventional approaches of manufacturing of cutting tools can require hundreds of operations to form a spherical reamer.

As shown in FIG. 11, stamped cutting panels can be formed by punching cavities in a flat sheet, forming holes for receiving bone chips, and setting panel curvature and teeth height. A center support, base, and dome can be formed and assembled with the panels to form a single cutting tool. Thus, for example, in some embodiments, the following steps can be taken:

1. The specific tooth cutting angle is punched into a flat metal blank with accuracy of 0.001±0.0005" as the first step. Angle can be set based on intended cutting requirements of the bone.
2. Punch opening for bone chips around tooth and create cutting edge.
3. Form spherical section from the flat metal blank and elevate all teeth above spherical surface with tooth elevation tolerance of ±0.002". Teeth are formed as contours of the intended spherical surfaces as opposed to just straight edges. The opening around the teeth can be further formed into funnels at specific angles to direct the bone chips away from the outer surface and into the hollow cavity of the cutter.
4. Multiple panels are formed (3 to 8 for example) which are assembled and laser welded together forming a spherical reamer.

Using the manufacturing techniques described herein, any number of teeth (e.g., 1-20 or more) can be made in a single forming step. In contrast, conventional systems require multiple forming steps for each individual tooth. Because the number of operations required to manufacture a spherical reamer can be greatly reduced, the costs are similarly reduced, thereby providing a lower cost, yet equally effective, cutting tool that can be removed from clinical service at a the end of its functional life without significant financial loss.

Figure 12:
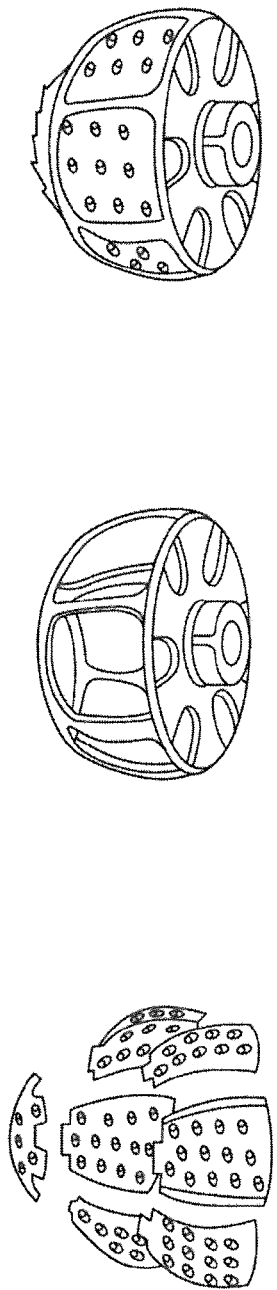
FIG. 12 illustrates a spherical reamer formed from panels coupled to a plastic molded part.

It should be understood that the supporting structure for the panels can be formed in various manners. For example, FIG. 12 illustrates an alternative approach in which the panels are secured by a plastic molded part.

Figure 13:
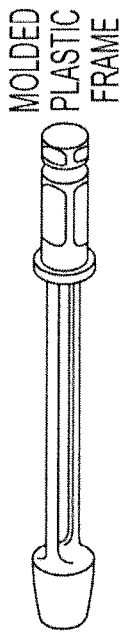
FIG. 13 illustrates a cylindrical reamer formed from panels coupled to a plastic molded part.

In some embodiments, the panels are placed directly into an injection molding tool and a medical grade plastic (e.g., PEI (polyetherimide, ULTEM®), PEEK (polyetheretherketone), PAI (polyamidide, TORLON®) can be injected around the periphery of the panels creating a frame that encloses and secures the panels. FIG. 13 illustrates a similar structure to that illustrated in FIG. 12; however, instead of a spherical reamer, FIG. 13 depicts a cylindrical reamer.

The cutting tools can be color coded to facilitate identification of the various sizes and types of cutting tools. When the cutting tool frames are formed by injection molding, such color coding can be achieved by varying the color of the injection molded plastic part.

Laboratory testing of a disclosed embodiment provided a comparison to existing art spherical reamers. Bovine bone specimens were used to monitor the speed to prepare a standard preparation, the temperature generated during that preparation and how many preparations could be completed before cutting edge damage generated a temperature exposure to the bone above 50° C. (122° F.). FIG. 12 summarizes the results of this testing and illustrates some of the improvements, such as the ability to cut bone at a lower temperature for a greater number of uses.

All cutting tools will eventually wear at the cutting edges resulting in a non-efficient cutter which would need to be sharpened or discarded. This is true of all industries including the medical field where these cutters are machining bone. In this field, the consequences of the cutter becoming dull and continuing to use it can result in bone necrosis. This in turn can jeopardize the success of the surgical procedure as the prosthesis must be supported by live, healthy bone to stabilize the implant. Excessive heat will kill the bone leading to bone resorption and a less than ideal interference fit between the bone and the implant. The rounding of the teeth cutting edges and damage to these edges can be demonstrated after 4-6 uses of these reamers in cow bone. It is for that reason all cutters should be qualified through laboratory testing to define the maximum number of uses under worst-case conditions which will not violate the temperature threshold for killing bone. This test result can then be used as a method to identify when the cutter should be removed from use.

Figure 14A:
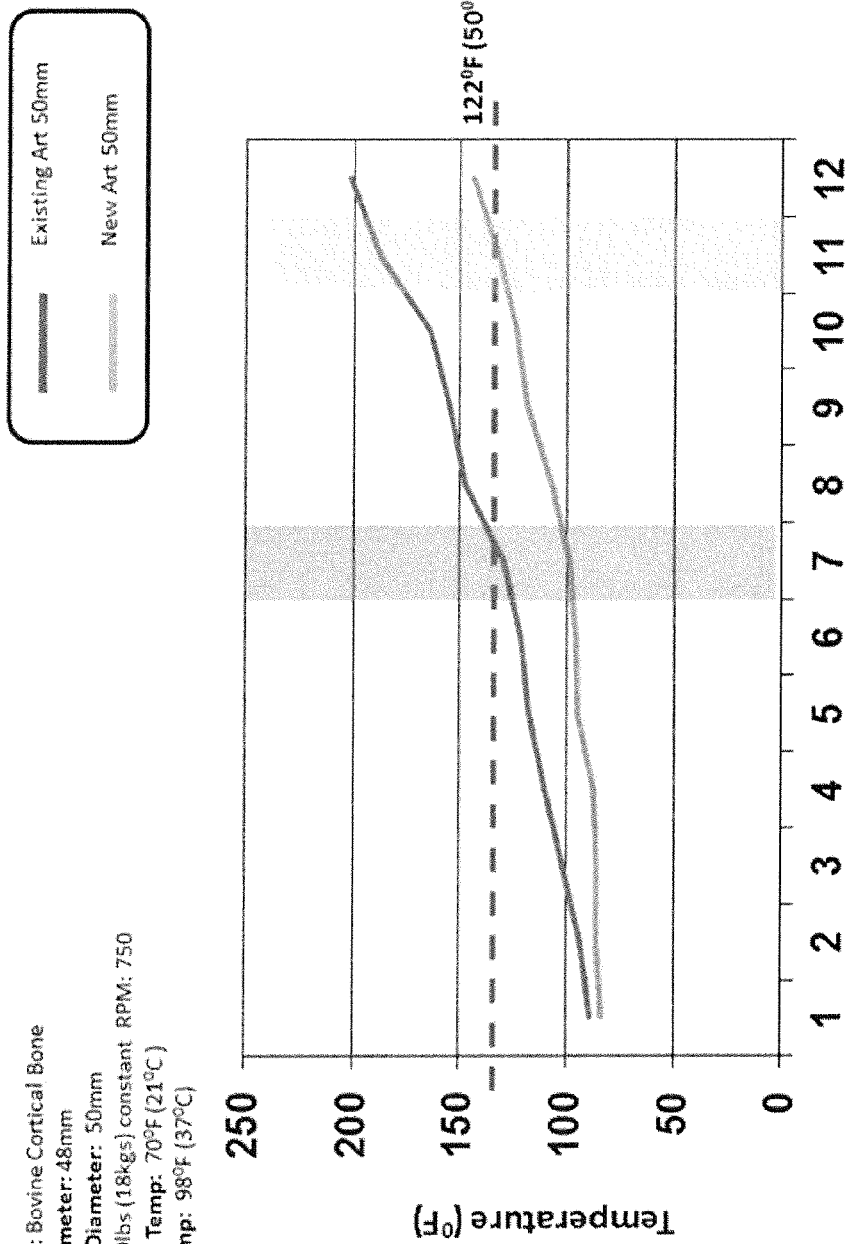
FIGS. 14A and B illustrate the results of an exemplary test procedure.
Figure 14B:
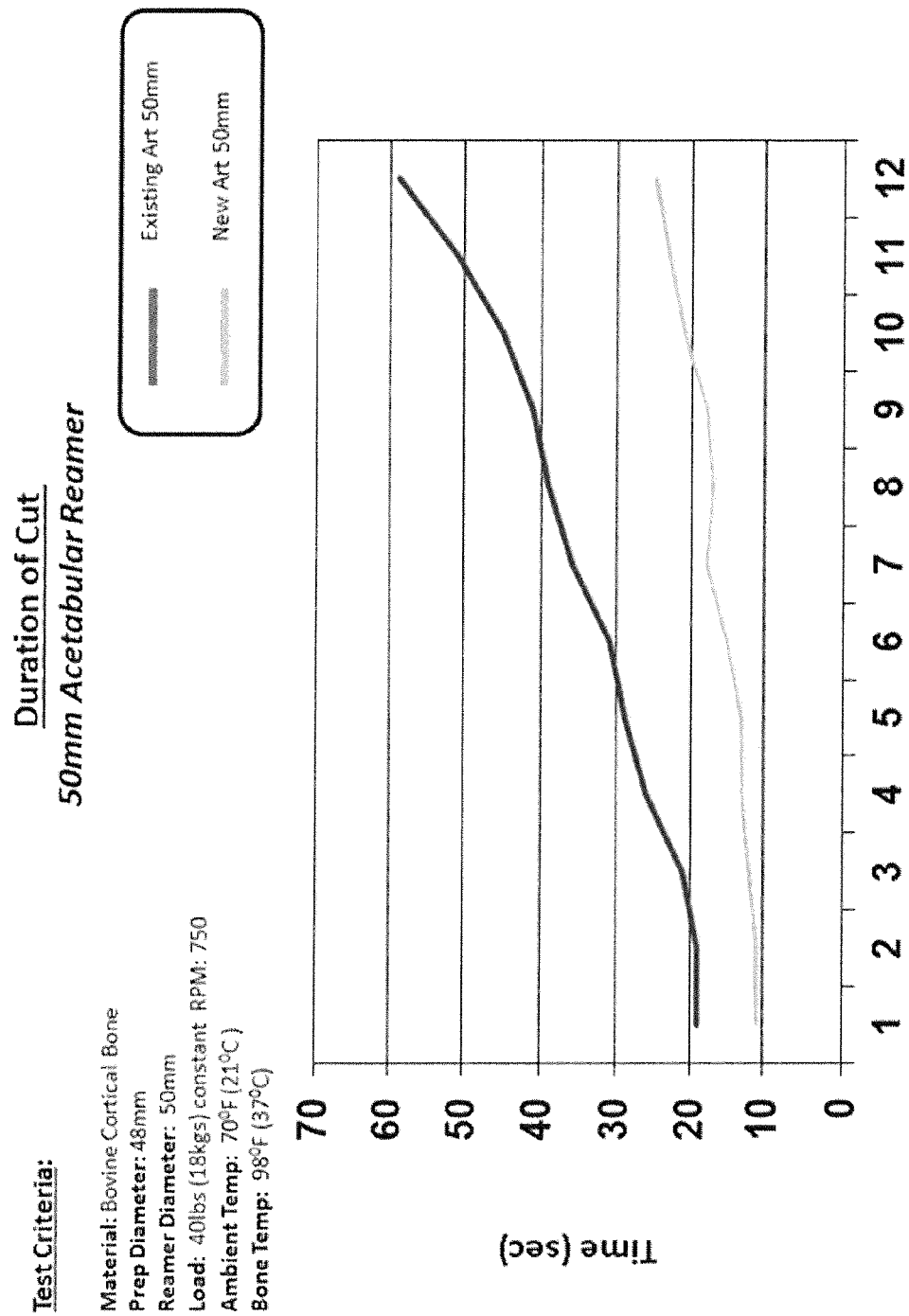
FIG. 14C illustrates a setup for the exemplary test procedure.
Figure 14C:
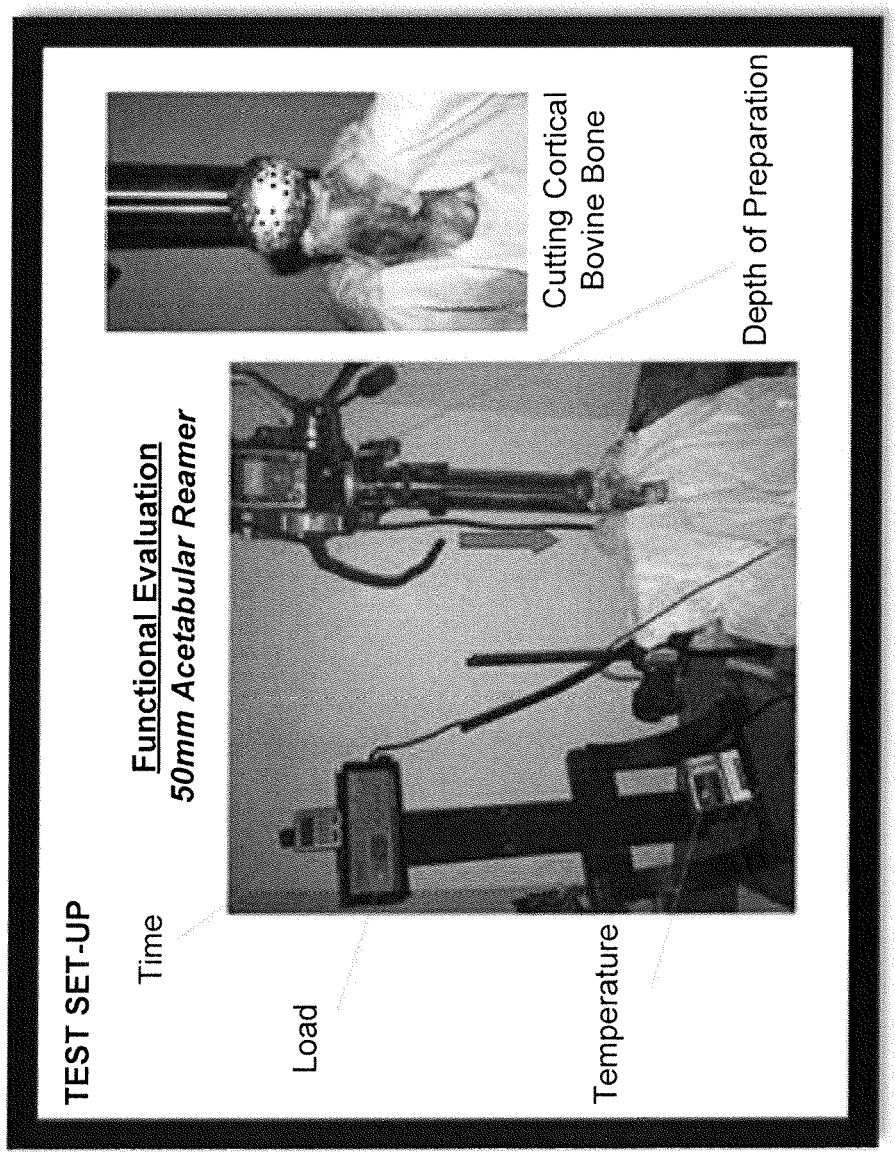

FIG. 14 illustrates a laboratory test set-up for determining the effective functional life of a cutting tool. In these tests, acetabular reamers were used to cut bone (i.e., cortical bovine bone) to determine the number of uses the acetabular reamers can experience before the end of their effective functional life. In one example, it was determined that approximately six (6) uses of the reamer produces a complete preparation without generating excessive heat (e.g., temperatures at or above 122° F. (50° C.)).

FIG. 14 also illustrates the results of an acetabular reamer evaluation in bovine bone, including (1) a chart showing the functional evaluation of a 50 mm acetabular reamer to cut bovine bone, graphing the number of bone preparations (i.e., uses of the cutting tool) and the temperature in the bone preparation area; and (2) a chart showing the functional evaluation of a 50 mm acetabular reamer to cut bovine bone, graphing the number of bone preparations (i.e., uses of the cutting tool) and the time required to achieve the bone preparation. As shown in FIG. 14, continuing to use the cutter after the sixth use consistently resulted in a longer preparation time and increased heat generation. The sharpness of the teeth cutting edges are directly proportional to the load required to advance the cutter, and therefore the resulting friction/heat generated. As the cutting edge rounds (or dulls), it becomes less effective in penetrating the surface of the bone and requires additional load to attempt to advance it. This cutter wear is generally consistent for all cutting tools.

Figure 15:
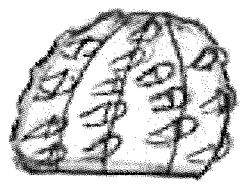
FIG. 15 illustrates exemplary cutting tools of at least some of the disclosed embodiments, including a spherical reamer, long bone tapered reamer, cylindrical reamer, and patellar reamer.
Figure 15:
Figure 15:
Figure 15:
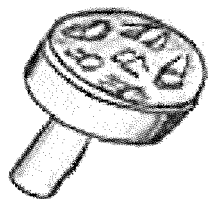

FIG. 15 illustrates exemplary cutting tools of at least some of the disclosed embodiments, including a spherical reamer, long bone tapered reamer, cylindrical reamer, and patellar reamer. The cutting tools and methods of manufacturing the same can provide a number of improvements, including (in certain embodiments) at least some of the following improvements:
1. Multiple teeth designs and teeth orientations to address multiple machining needs of the bone yielding a faster, cooler cut.
2. Tooth design geometries which address side cutting, end cutting and a combination of both.
3. A thinner material for forming the spherical reamer which can improve sharpness and reduction of heat.
4. A thinner material which also provides for more efficient forming of teeth and component parts improving manufacturing tool life.
5. Ability to produce multiple teeth designs and multiple teeth in fewer manufacturing steps.
6. A method of assembling a spherical reamer using multiple panels, pre-stamped with teeth of specific geometry and orientation.

The novel approach to producing more efficient medical reamers described herein can help ensure a proper bone preparation for every patient. In addition, the cutting tools described herein can provide improved sharpness, reduced heat during the reaming and a faster preparation based on tooth geometry and orientation. These improvements are also possible through a less expensive manufacturing process which makes it more economical to discard the reamer when it becomes dull.

Functional Life of Cutting Tools

It is also desirable to understand the effective functional life of the cutting tools described herein. As with any cutting tool, no matter how efficient the cutter has been designed, it will dull after multiple uses and its effective life will have terminated. Currently medical spherical reamers are used multiple times without any monitoring of the status of where the cutter is in its life cycle. Hospitals receive a new spherical reamer and follow an instrument processing procedure that includes cleaning, sterilizing, use, cleaning, sterilizing, and reuse. However, that cycle can continue for many, many surgical procedures before a surgeon notices the reamer is not cutting well.

Cutting teeth dull after even a few uses and dull cutting teeth generating heat that can be sufficient to cause bone necrosis. Accordingly, in addition to improving teeth design, it can also be helpful to provide the ability to indicate when a cutter should be removed from use to avoid issues relating to bone necrosis from dull cutters. In conventional approaches, instruments are used in hospitals on patients many times without knowledge of the life expectancy of the reamer and often beyond the functional life of the instrument. Some of the reluctance to discard the instrument after a single use is the cost of manufacturing these instruments. It is also perceived by the medical industry through orthopedic surgeons that these instruments do have a functional life greater than a single use. Accordingly, significant improvements in manufacturing costs, such as those realized by the embodiments described herein, can help to reduce the number of uses needed to obtain a return on investment.

As described above, the methods described herein can create more cost effective cutting tools, such as spherical reamers. In addition, the methods described herein can provide a means for defining the effective functional life of the cutting tools and providing a method of knowing when to discard it to ensure that the cutting tool used for any procedure (e.g., a total hip procedure) will be effective for its intended purpose.

In at least some of the embodiments described herein, as described above, novel medical reamers can include at least some of the following design parameters, enabling the production of more efficient tools for cutting bone:
1. Optimize forces applied to the reamer.
2. Thin, sharp tooth edge.
3. Specific tooth designs and tooth orientations providing a faster completion of the reaming cycle.
4. Adequate bone chip exit path to minimize friction from the flow of the chips at the cutter surface.
5. Minimize friction from cutting by using thinner materials and improved tooth geometry.

6. Define the functional life of the cutting edges through laboratory testing to know when to discard the reamer.
7. Provide an improved and efficient manufacturing process.

Laboratory testing to confirm an improved speed of the preparation, a lower cutting exposure temperature to the bone and an increased functional life to the reamer.

It should also be understood that these design principles can be incorporated into other cutting tools than those described in the figures, such as medical reamers that are used for patella resurfacing, glenoid reaming and machining the canal of long bones.

In view of the many possible embodiments to which the principles of the disclosed invention may be applied, it should be recognized that the illustrated embodiments are only preferred examples of the invention and should not be taken as limiting the scope of the invention.

We claim:

1. A method of forming a cutting tool comprising:
   forming a plurality of panels from one or more flat sheets of metal, the plurality of panels including a plurality of side panels and a dome member extending along a radial axis of the cutting tool;
   stamping the plurality of panels to form a plurality of cavities and punching holes at or adjacent to the plurality of cavities to provide a plurality of bone-chip-receiving openings and a plurality of cutting edges; and
   coupling the plurality of stamped panels to a frame member to form the cutting tool,
   wherein the frame member is formed with an elongated center member having a length extended along a longitudinal axis of the cutting tool fixed at one end to a base member extended along the radial axis and the act of coupling the plurality of stamped panels to the frame member comprises:
   securing the plurality of stamped side panels to the frame member so that the plurality of stamped side panels at least partially surround the elongated center member of the frame member along a portion of the length of the elongated center member, and
   securing the stamped dome member to the frame member so that the stamped dome member extends over an end of the elongated center member opposite the end fixed to the base member.

2. The method of claim 1, wherein the act of forming the plurality of cavities comprises forming a plurality of V-shaped cavities.

3. The method of claim 2, wherein the act of forming the plurality of panels further comprises stamping the one or more panels to create a desired height of the cutting edges and to provide a desired curvature of the one or more panels.

4. The method of claim 3, wherein the act of stamping the one or more panels to create a desired height of the cutting edges and to provide a desired curvature of the one or more panels is performed in a single stamping operation.

5. The method of claim 1, wherein the act of forming a plurality of side panels from one or more flat sheets of metal comprises forming the plurality of cutting edges with different zones that have cutting edges with different characteristics, the different zones comprising a polar zone, a transition zone, and an equatorial zone.

6. The method of claim 5, wherein respective cutting edges each define a cutting angle between the cutting edge and a perpendicular surface to a first side of the cutting tool, and the cutting angle between cutting edges in the polar zone are larger than those defined by cutting edges in the transition zone, and the cutting angle between cutting edges in the transition zone are larger than those defined by cutting edges in the equatorial zone.

7. The method of claim 1, wherein respective panels have cutting edges with orientation angles that vary along the respective panel.

8. The method of claim 1, wherein the act of securing the plurality of stamped panels to the frame member comprises laser welding.

9. The method of claim 1, wherein the act of coupling the plurality of stamped panels to the frame member comprises: placing the plurality of stamped panels into an injection molding tool; and injection molding the frame member around the plurality of stamped panels to create the frame member.

10. The method of claim 1, wherein the one or more flat sheets of metal have a thickness less than 0.040 inches.

11. The method of claim 1, wherein the act of punching holes at or adjacent to the plurality of cavity comprises forming bone-chip-receiving openings with a funnel angle that is between 20 and 40 degrees.

12. The method of claim 1, wherein the cutting tool comprises a hollow spherical reamer, a hollow tapered reamer, or a hollow cylindrical reamer.

13. The method of claim 1, further comprising:
    determining an effective functional life of the cutting tool.

14. The method of claim 1, wherein, when coupled to the frame member, the plurality of stamped panels define a plurality of latitude lines about the axis of rotation of the cutting tool and the plurality of formed cutting edges have orientation angles relative to the latitude lines that vary.

* * * * *